United States Patent
Berckmans, III et al.

(10) Patent No.: US 8,221,121 B2
(45) Date of Patent: *Jul. 17, 2012

(54) METHOD FOR PRE-OPERATIVE VISUALIZATION OF INSTRUMENTATION USED WITH A SURGICAL GUIDE FOR DENTAL IMPLANT PLACEMENT

(75) Inventors: Bruce Berckmans, III, Palm Beach Gardens, FL (US); Zachary B. Suttin, West Palm Beach, FL (US)

(73) Assignee: Biomet 3i, LLC, Palm Beach Gardens, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/179,609

(22) Filed: Jul. 11, 2011

(65) Prior Publication Data

US 2011/0269104 A1    Nov. 3, 2011

Related U.S. Application Data

(63) Continuation of application No. 12/425,202, filed on Apr. 16, 2009.

(60) Provisional application No. 61/124,331, filed on Apr. 16, 2008.

(51) Int. Cl.
*A61C 5/00* (2006.01)
(52) U.S. Cl. ........................................ 433/215
(58) Field of Classification Search ............... 433/75, 433/76, 215; 700/97, 98
See application file for complete search history.

(56) References Cited

U.S. PATENT DOCUMENTS

| | | | |
|---|---|---|---|
| 3,906,634 A | 9/1975 | Aspel | |
| 3,919,772 A | 11/1975 | Lenczycki | 433/173 |
| 3,958,471 A | 5/1976 | Muller | 82/1.11 |
| 4,011,602 A | 3/1977 | Rybicki et al. | 623/23.76 |
| 4,056,585 A | 11/1977 | Waltke | 433/74 |
| 4,086,701 A | 5/1978 | Kawahara et al. | 433/174 |
| 4,177,562 A | 12/1979 | Miller et al. | 433/174 |
| 4,294,544 A | 10/1981 | Altschuler et al. | 356/610 |

(Continued)

FOREIGN PATENT DOCUMENTS

DE    10029256    11/2000

(Continued)

OTHER PUBLICATIONS

Biomet 3i Navigator™ "Navigator™ System for CT Guided Surgery Manual," pp. 1-26, Oct. 2007.

(Continued)

*Primary Examiner* — Cris L Rodriguez
*Assistant Examiner* — Eric Rosen
(74) *Attorney, Agent, or Firm* — Nixon Peabody LLP

(57) ABSTRACT

The invention relates to manufacturing a surgical guide to be placed in a patient's mouth. The patient's mouth is scanned to obtain surgical-region scan data at a region where an implant is to be located. The patient's mouth is also scanned in the opened position to acquire dental conditions opposite from the surgical region so as to obtain opposing-condition scan data. A virtual model is developed using the surgical-region scan data and the opposing-condition scan data. Using the virtual model, a surgical plan is developed that includes the location of the implant to be installed in the patient. A virtual surgical guide is also developed based on the surgical plan. The dimensions of instrumentation to be used with the surgical guide are checked to ensure they will fit within the mouth by use of the opposing-condition scan data. After checking, final surgical-guide manufacturing information is obtained for manufacturing the surgical guide.

23 Claims, 8 Drawing Sheets

U.S. PATENT DOCUMENTS

| | | | |
|---|---|---|---|
| 4,306,862 A | 12/1981 | Knox | 433/77 |
| 4,325,373 A | 4/1982 | Slivenko et al. | |
| 4,341,312 A | 7/1982 | Scholer | 211/70.6 |
| 4,364,381 A | 12/1982 | Sher et al. | |
| 4,439,152 A | 3/1984 | Small | |
| 4,543,953 A | 10/1985 | Slocum et al. | |
| 4,547,157 A | 10/1985 | Driskell | 433/173 |
| 4,571,180 A | 2/1986 | Kulick | |
| 4,611,288 A | 9/1986 | Duret | 700/163 |
| 4,624,673 A | 11/1986 | Meyer | 433/173 |
| 4,663,720 A | 5/1987 | Duret | 700/163 |
| 4,713,004 A | 12/1987 | Linkow et al. | 433/174 |
| 4,756,689 A | 7/1988 | Lundgren et al. | |
| 4,758,161 A | 7/1988 | Niznick | 433/173 |
| 4,767,331 A | 8/1988 | Hoe | 433/213 |
| 4,772,204 A | 9/1988 | Soderberg | 433/174 |
| 4,821,200 A | 4/1989 | Oberg | 700/182 |
| 4,842,518 A | 6/1989 | Linkow et al. | 433/174 |
| 4,850,870 A | 7/1989 | Lazzara et al. | 433/174 |
| 4,850,873 A | 7/1989 | Lazzara et al. | 433/220 |
| 4,854,872 A | 8/1989 | Detsch | 433/173 |
| 4,856,994 A | 8/1989 | Lazzara et al. | 433/173 |
| 4,872,839 A | 10/1989 | Brajnovic | |
| 4,906,191 A | 3/1990 | Soderberg | 433/213 |
| 4,906,420 A | 3/1990 | Brajnovic et al. | |
| 4,931,016 A | 6/1990 | Sillard | |
| 4,935,635 A | 6/1990 | O'Harra | 250/559.06 |
| 4,961,674 A | 10/1990 | Wang et al. | |
| 4,964,770 A | 10/1990 | Steinbichler et al. | 433/223 |
| 4,986,753 A | 1/1991 | Sellers | |
| 4,988,297 A | 1/1991 | Lazzara et al. | |
| 4,998,881 A | 3/1991 | Lauks | |
| 5,000,685 A | 3/1991 | Brajnovic | |
| 5,006,069 A | 4/1991 | Lazzara et al. | 433/173 |
| 5,015,183 A | 5/1991 | Fenick | |
| 5,015,186 A | 5/1991 | Detsch | |
| 5,030,096 A | 7/1991 | Hurson et al. | 433/173 |
| 5,035,619 A | 7/1991 | Daftary | 433/173 |
| 5,040,982 A | 8/1991 | Stefan-Dogar | |
| 5,040,983 A | 8/1991 | Binon | 433/173 |
| 5,064,375 A | 11/1991 | Jorneus | 433/229 |
| 5,071,351 A | 12/1991 | Green, Jr. et al. | 433/173 |
| 5,073,111 A | 12/1991 | Daftary | 433/173 |
| 5,087,200 A | 2/1992 | Brajnovic et al. | |
| 5,100,323 A | 3/1992 | Friedman et al. | 433/173 |
| 5,104,318 A | 4/1992 | Piche et al. | 433/174 |
| 5,106,300 A | 4/1992 | Voitik | 433/173 |
| 5,122,059 A | 6/1992 | Durr et al. | 433/173 |
| 5,125,839 A | 6/1992 | Ingber et al. | 433/169 |
| 5,125,841 A | 6/1992 | Carlsson et al. | 433/213 |
| 5,133,660 A | 7/1992 | Fenick | |
| 5,135,395 A | 8/1992 | Marlin | 433/174 |
| 5,145,371 A | 9/1992 | Jorneus | 433/173 |
| 5,145,372 A | 9/1992 | Daftary | 433/173 |
| 5,176,516 A | 1/1993 | Koizumi | |
| 5,188,800 A | 2/1993 | Green, Jr. et al. | 134/1 |
| 5,195,892 A | 3/1993 | Gersberg | 433/174 |
| 5,205,745 A | 4/1993 | Kamiya et al. | 433/173 |
| 5,209,659 A | 5/1993 | Friedman et al. | 433/173 |
| 5,209,666 A | 5/1993 | Balfour et al. | 433/173 |
| 5,213,502 A | 5/1993 | Daftary | 433/172 |
| 5,237,998 A | 8/1993 | Duret et al. | 600/476 |
| 5,246,370 A | 9/1993 | Coatoam | |
| 5,257,184 A | 10/1993 | Mushabac | 433/75 |
| 5,281,140 A | 1/1994 | Niznick | 433/172 |
| 5,286,195 A | 2/1994 | Clostermann | 433/172 |
| 5,286,196 A | 2/1994 | Brajnovic et al. | |
| 5,292,252 A | 3/1994 | Nickerson et al. | 433/173 |
| 5,297,963 A | 3/1994 | Dafatry | 433/172 |
| 5,302,125 A | 4/1994 | Kownacki et al. | |
| 5,312,254 A | 5/1994 | Rosenlicht | 433/173 |
| 5,312,409 A | 5/1994 | McLaughlin et al. | |
| 5,316,476 A | 5/1994 | Krauser | 433/173 |
| 5,320,529 A | 6/1994 | Pompa | |
| 5,328,371 A | 7/1994 | Hund et al. | |
| 5,334,024 A | 8/1994 | Niznick | 433/173 |
| 5,336,090 A | 8/1994 | Wilson, Jr. et al. | 433/172 |
| 5,338,196 A | 8/1994 | Beaty et al. | 433/172 |
| 5,338,198 A | 8/1994 | Wu et al. | 433/213 |
| 5,343,391 A | 8/1994 | Mushabac | 433/76 |
| 5,344,457 A | 9/1994 | Pilliar et al. | 606/60 |
| 5,350,297 A | 9/1994 | Cohen | |
| 5,359,511 A | 10/1994 | Schroeder et al. | 433/75 |
| 5,362,234 A | 11/1994 | Salazar et al. | 433/169 |
| 5,362,235 A | 11/1994 | Daftary | 433/172 |
| 5,368,483 A | 11/1994 | Sutter et al. | 433/173 |
| 5,370,692 A | 12/1994 | Fink et al. | 128/898 |
| 5,372,502 A | 12/1994 | Massen et al. | 433/215 |
| 5,386,292 A | 1/1995 | Massen et al. | 356/603 |
| 5,413,481 A | 5/1995 | Goppel et al. | 433/214 |
| 5,417,569 A | 5/1995 | Perisse | |
| 5,417,570 A | 5/1995 | Zuest et al. | 433/177 |
| 5,419,702 A | 5/1995 | Beaty et al. | 433/214 |
| 5,431,567 A | 7/1995 | Daftary | 433/172 |
| 5,437,551 A | 8/1995 | Chalifoux | 433/173 |
| 5,440,393 A | 8/1995 | Wenz | 356/611 |
| 5,452,219 A | 9/1995 | Dehoff et al. | 700/163 |
| 5,458,488 A | 10/1995 | Chalifoux | 433/173 |
| 5,476,382 A | 12/1995 | Daftary | 433/172 |
| 5,476,383 A | 12/1995 | Beaty et al. | 433/214 |
| 5,492,471 A | 2/1996 | Singer | 433/172 |
| 5,516,288 A | 5/1996 | Sichler et al. | |
| 5,527,182 A | 6/1996 | Willoughby | |
| 5,533,898 A | 7/1996 | Mena | 433/173 |
| 5,538,426 A | 7/1996 | Harding et al. | 433/172 |
| 5,547,377 A | 8/1996 | Daftary | 433/172 |
| 5,556,278 A | 9/1996 | Meitner | |
| 5,564,921 A | 10/1996 | Marlin | 433/172 |
| 5,564,924 A | 10/1996 | Kwan | 433/173 |
| 5,569,578 A | 10/1996 | Mushabac | 433/215 |
| 5,575,656 A | 11/1996 | Hajjar | |
| 5,580,244 A | 12/1996 | White | 433/37 |
| 5,580,246 A | 12/1996 | Fried et al. | |
| 5,595,703 A | 1/1997 | Swaelens | 264/401 |
| 5,613,852 A | 3/1997 | Bavitz | |
| 5,630,717 A | 5/1997 | Zuest et al. | |
| 5,636,986 A | 6/1997 | Pezeshkian | |
| 5,651,675 A | 7/1997 | Singer | 433/172 |
| 5,652,709 A | 7/1997 | Andersson | 700/161 |
| 5,658,147 A | 8/1997 | Phimmasone | 433/213 |
| 5,662,476 A | 9/1997 | Ingber et al. | |
| 5,674,069 A | 10/1997 | Osorio | 433/172 |
| 5,674,071 A | 10/1997 | Beaty et al. | 433/172 |
| 5,674,073 A | 10/1997 | Ingber et al. | 433/213 |
| 5,681,167 A | 10/1997 | Lazarof | 433/174 |
| 5,685,715 A | 11/1997 | Beaty et al. | 433/173 |
| 5,688,283 A | 11/1997 | Knapp | |
| 5,704,936 A | 1/1998 | Mazel | |
| 5,718,579 A | 2/1998 | Kennedy | |
| 5,725,376 A | 3/1998 | Poirier | |
| 5,733,124 A | 3/1998 | Kwan | |
| 5,741,215 A | 4/1998 | D'Urso | 600/407 |
| 5,743,916 A | 4/1998 | Greenberg et al. | |
| 5,759,036 A | 6/1998 | Hinds | 433/214 |
| 5,762,125 A | 6/1998 | Mastrorio | 164/4.1 |
| 5,762,500 A | 6/1998 | Lazarof | |
| 5,768,134 A | 6/1998 | Swaelens et al. | |
| 5,769,636 A | 6/1998 | Di Sario | |
| 5,791,902 A | 8/1998 | Lauks | |
| 5,800,168 A | 9/1998 | Cascione et al. | |
| 5,813,858 A | 9/1998 | Singer | 433/173 |
| 5,823,778 A | 10/1998 | Schmitt | 433/214 |
| 5,842,859 A | 12/1998 | Palacci | |
| 5,846,079 A | 12/1998 | Knode | |
| 5,851,115 A | 12/1998 | Carlsson et al. | 433/215 |
| 5,857,853 A | 1/1999 | van Nifterick et al. | 433/213 |
| 5,871,358 A | 2/1999 | Ingber et al. | |
| 5,873,722 A | 2/1999 | Lazzara et al. | 433/173 |
| 5,876,204 A | 3/1999 | Day et al. | |
| 5,885,078 A | 3/1999 | Cagna et al. | |
| 5,888,034 A | 3/1999 | Greenberg | |
| 5,904,483 A | 5/1999 | Wade | |
| 5,915,962 A | 6/1999 | Rosenlicht | |
| 5,927,982 A | 7/1999 | Kruger | |
| 5,938,443 A | 8/1999 | Lazzara et al. | 433/173 |
| 5,954,769 A | 9/1999 | Rosenlicht | |
| 5,964,591 A | 10/1999 | Beaty et al. | |

| | | |
|---|---|---|
| 5,967,777 A | 10/1999 | Klein et al. |
| 5,984,681 A | 11/1999 | Huang |
| 5,989,025 A | 11/1999 | Conley |
| 5,989,029 A | 11/1999 | Osorio et al. .................. 433/173 |
| 5,989,258 A | 11/1999 | Hattori |
| 5,997,681 A | 12/1999 | Kinzie ........................... 156/263 |
| 6,000,939 A | 12/1999 | Ray et al. |
| 6,008,905 A | 12/1999 | Breton et al. .................. 356/402 |
| 6,068,479 A | 5/2000 | Kwan |
| 6,099,311 A | 8/2000 | Wagner et al. |
| 6,099,313 A | 8/2000 | Dorken et al. |
| 6,099,314 A | 8/2000 | Kopelman et al. ............ 433/213 |
| 6,120,293 A | 9/2000 | Lazzara et al. ................. 433/173 |
| 6,129,548 A | 10/2000 | Lazzara et al. ................. 433/172 |
| 6,135,773 A | 10/2000 | Lazzara |
| 6,142,782 A | 11/2000 | Lazarof |
| 6,174,168 B1 | 1/2001 | Dehoff et al. ............... 433/202.1 |
| 6,175,413 B1 | 1/2001 | Lucas ........................... 356/614 |
| 6,190,169 B1 | 2/2001 | Bluemli et al. |
| 6,197,410 B1 | 3/2001 | Vallittu et al. |
| 6,200,125 B1 | 3/2001 | Akutagawa .................... 425/462 |
| 6,206,693 B1 | 3/2001 | Hultgren ........................ 433/38 |
| 6,210,162 B1 | 4/2001 | Chishti et al. ................. 433/213 |
| 6,217,334 B1 | 4/2001 | Hultgren ....................... 433/215 |
| 6,227,859 B1 | 5/2001 | Sutter |
| 6,283,753 B1 | 9/2001 | Willoughby ................... 433/172 |
| 6,287,119 B1 | 9/2001 | Van Nifterick et al. |
| 6,296,483 B1 | 10/2001 | Champleboux |
| 6,319,000 B1 | 11/2001 | Branemark |
| 6,322,728 B1 | 11/2001 | Brodkin et al. ................. 264/19 |
| 6,382,975 B1 | 5/2002 | Poirier |
| 6,402,707 B1 | 6/2002 | Ernst ............................. 600/590 |
| 6,488,503 B1 | 12/2002 | Lichkus et al. ................ 433/202 |
| 6,497,574 B1 | 12/2002 | Miller ........................... 433/213 |
| 6,540,784 B2 | 4/2003 | Barlow et al. ............... 623/16.11 |
| 6,568,936 B2 | 5/2003 | MacDougald et al. |
| 6,575,751 B1 | 6/2003 | Lehmann et al. .............. 433/223 |
| 6,594,539 B1 | 7/2003 | Geng .............................. 700/117 |
| 6,610,079 B1 | 8/2003 | Li et al. |
| 6,619,958 B2 | 9/2003 | Beaty et al. .................... 433/173 |
| 6,629,840 B2 | 10/2003 | Chishti et al. .................. 433/24 |
| 6,634,883 B2 | 10/2003 | Ranalli |
| 6,648,640 B2 | 11/2003 | Rubbert et al. ................ 433/24 |
| 6,671,539 B2 | 12/2003 | Gateno et al. ................. 600/426 |
| 6,672,870 B2 | 1/2004 | Knapp |
| 6,688,887 B2 | 2/2004 | Morgan |
| 6,691,764 B2 | 2/2004 | Embert et al. .................. 164/4.1 |
| 6,743,491 B2 | 6/2004 | Cirincione et al. |
| 6,755,652 B2 | 6/2004 | Nanni |
| 6,772,026 B2 | 8/2004 | Bradbury et al. ............... 700/98 |
| 6,776,614 B2 | 8/2004 | Wiechmann et al. ........... 433/24 |
| 6,783,359 B2 | 8/2004 | Kapit |
| 6,790,040 B2 | 9/2004 | Amber et al. .................. 433/173 |
| 6,793,491 B2 | 9/2004 | Klein et al. |
| 6,808,659 B2 | 10/2004 | Schulman et al. .............. 264/16 |
| 6,814,575 B2 | 11/2004 | Poirier |
| 6,821,462 B2 | 11/2004 | Schulman et al. .............. 264/16 |
| 6,829,498 B2 | 12/2004 | Kipke et al. ................... 600/378 |
| D503,804 S | 4/2005 | Phleps et al. |
| 6,882,894 B2 | 4/2005 | Durbin et al. .................. 700/118 |
| 6,885,464 B1 | 4/2005 | Pfeiffer et al. |
| 6,902,401 B2 | 6/2005 | Jorneus |
| 6,913,463 B2 | 7/2005 | Blacklock |
| 6,926,442 B2 | 8/2005 | Stöckl |
| 6,926,525 B1 | 8/2005 | Ronrig et al. |
| 6,939,489 B2 | 9/2005 | Moszner et al. ................ 264/16 |
| 6,942,699 B2 | 9/2005 | Stone et al. |
| 6,953,383 B2 | 10/2005 | Rothenberger |
| 6,957,118 B2 | 10/2005 | Kopelman et al. ............ 700/118 |
| 6,966,772 B2 | 11/2005 | Malin et al. |
| 6,970,760 B2 | 11/2005 | Wolf et al. .................... 700/163 |
| 6,971,877 B2 | 12/2005 | Harter |
| 6,994,549 B2 | 2/2006 | Brodkin et al. ............... 433/202.1 |
| 7,010,150 B1 | 3/2006 | Pfeiffer et al. |
| 7,010,153 B2 | 3/2006 | Zimmermann |
| 7,012,988 B2 | 3/2006 | Adler et al. |
| 7,018,207 B2 | 3/2006 | Prestipino |
| 7,021,934 B2 | 4/2006 | Aravena |
| 7,029,275 B2 | 4/2006 | Rubbert et al. ................. 433/24 |
| 7,044,735 B2 | 5/2006 | Malin |
| 7,056,115 B2 | 6/2006 | Phan et al. ...................... 433/24 |
| 7,056,472 B1 | 6/2006 | Behringer |
| 7,059,856 B2 | 6/2006 | Marotta |
| 7,066,736 B2 | 6/2006 | Kumar et al. |
| 7,084,868 B2 | 8/2006 | Farag et al. |
| 7,086,860 B2 | 8/2006 | Schuman et al. |
| 7,097,451 B2 | 8/2006 | Tang |
| 7,104,795 B2 | 9/2006 | Dadi |
| 7,110,844 B2 | 9/2006 | Kopelman et al. ............ 700/118 |
| 7,112,065 B2 | 9/2006 | Kopelman et al. ............ 433/213 |
| 7,118,375 B2 | 10/2006 | Durbin et al. .................. 433/68 |
| D532,991 S | 12/2006 | Gozzi |
| 7,153,132 B2 | 12/2006 | Tedesco |
| 7,153,135 B1 | 12/2006 | Thomas ....................... 433/213 |
| 7,163,443 B2 | 1/2007 | Basler et al. |
| 7,175,434 B2 | 2/2007 | Brajnovic |
| 7,175,435 B2 | 2/2007 | Andersson et al. |
| 7,178,731 B2 | 2/2007 | Basler |
| 7,214,062 B2 | 5/2007 | Morgan |
| 7,220,124 B2 | 5/2007 | Taub et al. .................... 433/213 |
| 7,228,191 B2 | 6/2007 | Hofmeister et al. ............ 700/98 |
| 7,236,842 B2 | 6/2007 | Kopelman et al. .............. 700/98 |
| 7,281,927 B2 | 10/2007 | Marotta |
| 7,286,954 B2 | 10/2007 | Kopelman et al. ............ 702/152 |
| 7,303,420 B2 | 12/2007 | Huch et al. |
| 7,319,529 B2 | 1/2008 | Babayoff ...................... 356/601 |
| 7,322,746 B2 | 1/2008 | Beckhaus et al. |
| 7,322,824 B2 | 1/2008 | Schmitt ........................ 433/215 |
| 7,324,680 B2 | 1/2008 | Zimmermann |
| 7,329,122 B1 | 2/2008 | Scott |
| 7,333,874 B2 | 2/2008 | Taub et al. .................... 700/117 |
| 7,335,876 B2 | 2/2008 | Eiff et al. |
| D565,184 S | 3/2008 | Royzen |
| 7,367,801 B2 | 5/2008 | Saliger |
| 7,379,584 B2 | 5/2008 | Rubbert et al. ................ 382/154 |
| D571,471 S | 6/2008 | Stöckl |
| 7,381,191 B2 | 6/2008 | Fallah |
| 7,383,094 B2 | 6/2008 | Kopelman et al. ............ 700/118 |
| D575,747 S | 8/2008 | Abramovich et al. |
| 7,421,608 B2 | 9/2008 | Schron |
| 7,429,175 B2 | 9/2008 | Gittelson |
| 7,435,088 B2 | 10/2008 | Brajnovic |
| 7,476,100 B2 | 1/2009 | Kuo ................................. 433/6 |
| 7,481,647 B2 | 1/2009 | Sambu et al. ................. 425/436 |
| 7,488,174 B2 | 2/2009 | Kopelman et al. ............ 433/213 |
| 7,497,619 B2 | 3/2009 | Stoeckl |
| 7,497,983 B2 | 3/2009 | Khan et al. .................... 264/673 |
| 7,520,747 B2 | 4/2009 | Stonisch |
| 7,522,764 B2 | 4/2009 | Schwotzer |
| 7,534,266 B2 | 5/2009 | Kluger |
| 7,536,234 B2 | 5/2009 | Kopelman et al. ............ 700/118 |
| 7,545,372 B2 | 6/2009 | Kopelman et al. ............ 345/419 |
| 7,551,760 B2 | 6/2009 | Scharlack et al. |
| 7,555,403 B2 | 6/2009 | Kopelman et al. ............ 702/152 |
| 7,556,496 B2 | 7/2009 | Cinader, Jr. et al. ............ 433/24 |
| 7,559,692 B2 | 7/2009 | Beckhaus et al. |
| 7,563,397 B2 | 7/2009 | Schulman et al. .............. 264/16 |
| D597,769 S | 8/2009 | Richter et al. |
| 7,572,058 B2 | 8/2009 | Pruss et al. |
| 7,572,125 B2 | 8/2009 | Brajnovic |
| 7,574,025 B2 | 8/2009 | Feldman |
| 7,578,673 B2 | 8/2009 | Wen et al. ....................... 433/24 |
| 7,580,502 B2 | 8/2009 | Dalpiaz et al. |
| 7,581,951 B2 | 9/2009 | Lehmann et al. |
| 7,582,855 B2 | 9/2009 | Pfeiffer |
| 7,628,537 B2 | 12/2009 | Schulze-Ganzlin |
| 7,632,097 B2 | 12/2009 | Clerck ........................... 433/215 |
| 7,653,455 B2 | 1/2010 | Cinader, Jr. |
| 7,654,823 B2 | 2/2010 | Dadi |
| 7,655,586 B1 | 2/2010 | Brodkin et al. ................ 501/103 |
| 7,658,610 B2 | 2/2010 | Knopp ............................ 433/24 |
| 7,665,989 B2 | 2/2010 | Brajnovic et al. |
| 7,679,723 B2 | 3/2010 | Schwotzer |
| 7,687,754 B2 | 3/2010 | Eiff et al. |
| 7,689,308 B2 | 3/2010 | Holzner et al. |
| D614,210 S | 4/2010 | Basler et al. |
| 7,698,014 B2 | 4/2010 | Dunne et al. |
| 7,774,084 B2 | 8/2010 | Cinader, Jr. |

| | | |
|---|---|---|
| 7,780,907 B2 | 8/2010 | Schmidt et al. |
| 7,785,007 B2 | 8/2010 | Stoeckl |
| 7,787,132 B2 | 8/2010 | Körner et al. |
| 7,796,811 B2 | 9/2010 | Orth et al. |
| 7,798,708 B2 | 9/2010 | Erhardt et al. |
| 7,801,632 B2 | 9/2010 | Orth et al. |
| 7,815,371 B2 | 10/2010 | Schulze-Ganzlin |
| 7,824,181 B2 | 11/2010 | Sers |
| D629,908 S | 12/2010 | Jerger et al. |
| 7,855,354 B2 | 12/2010 | Eiff |
| 7,865,261 B2 | 1/2011 | Pfeiffer |
| 7,876,877 B2 | 1/2011 | Stockl |
| 7,901,209 B2 | 3/2011 | Saliger et al. |
| 7,982,731 B2 | 7/2011 | Orth et al. |
| 7,985,119 B2 | 7/2011 | Basler et al. |
| 7,986,415 B2 | 7/2011 | Thiel et al. |
| 8,026,943 B2 | 9/2011 | Weber et al. |
| 8,038,440 B2 | 10/2011 | Swaelens et al. |
| 8,047,895 B2 | 11/2011 | Basler |
| 8,057,912 B2 | 11/2011 | Basler et al. |
| 8,062,034 B2 | 11/2011 | Hanisch et al. |
| 8,083,522 B2 | 12/2011 | Karkar et al. |
| 2001/0008751 A1 | 7/2001 | Chishti et al. |
| 2001/0034010 A1 | 10/2001 | MacDougald et al. ....... 433/223 |
| 2002/0010568 A1 | 1/2002 | Rubbert et al. .................... 703/6 |
| 2002/0028418 A1 | 3/2002 | Farag et al. ..................... 433/29 |
| 2002/0160337 A1 | 10/2002 | Klein et al. |
| 2002/0167100 A1 | 11/2002 | Moszner et al. ................. 264/16 |
| 2003/0130605 A1 | 7/2003 | Besek |
| 2003/0222366 A1 | 12/2003 | Stangel et al. ................... 264/16 |
| 2004/0029074 A1 | 2/2004 | Brajnovic |
| 2004/0048227 A1 | 3/2004 | Brajnovic |
| 2004/0219477 A1 | 11/2004 | Harter |
| 2004/0219479 A1 | 11/2004 | Malin et al. |
| 2004/0219490 A1 | 11/2004 | Gartner et al. ................. 433/218 |
| 2004/0220691 A1 | 11/2004 | Hofmeister et al. ............ 700/98 |
| 2004/0243481 A1 | 12/2004 | Bradbury et al. ................ 705/26 |
| 2004/0259051 A1 | 12/2004 | Brajnovic |
| 2005/0023710 A1 | 2/2005 | Brodkin et al. .................. 264/16 |
| 2005/0056350 A1 | 3/2005 | Dolabdjian et al. .......... 148/512 |
| 2005/0070782 A1 | 3/2005 | Brodkin ........... 600/407 |
| 2005/0084144 A1 | 4/2005 | Feldman ..................... 382/128 |
| 2005/0100861 A1 | 5/2005 | Choi |
| 2005/0170311 A1 | 8/2005 | Tardieu et al. |
| 2005/0271996 A1 | 12/2005 | Sporbert et al. ................. 433/24 |
| 2005/0277089 A1 | 12/2005 | Brajnovic |
| 2005/0277090 A1 | 12/2005 | Anderson et al. |
| 2005/0277091 A1 | 12/2005 | Andersson et al. |
| 2005/0282106 A1 | 12/2005 | Sussman et al. |
| 2005/0283065 A1 | 12/2005 | Babayoff ..................... 600/407 |
| 2006/0006561 A1 | 1/2006 | Brajnovic |
| 2006/0008763 A1 | 1/2006 | Brajnovic |
| 2006/0008770 A1 | 1/2006 | Brajnovic et al. |
| 2006/0093988 A1 | 5/2006 | Swaelens et al. |
| 2006/0094951 A1 | 5/2006 | Dean et al. ..................... 600/407 |
| 2006/0127848 A1 | 6/2006 | Sogo et al. |
| 2006/0210949 A1 | 9/2006 | Stoop |
| 2006/0263741 A1 | 11/2006 | Imgrund et al. ................. 433/24 |
| 2006/0281041 A1 | 12/2006 | Rubbert et al. ................. 433/24 |
| 2007/0015111 A1 | 1/2007 | Kopelman et al. ............ 433/213 |
| 2007/0031790 A1 | 2/2007 | Raby et al. .................... 433/213 |
| 2007/0065777 A1 | 3/2007 | Becker |
| 2007/0077532 A1 | 4/2007 | Harter |
| 2007/0092854 A1 | 4/2007 | Powell et al. ................. 433/213 |
| 2007/0141525 A1 | 6/2007 | Cinader, Jr. et al. ............ 433/23 |
| 2007/0211081 A1 | 9/2007 | Quadling et al. ............. 345/632 |
| 2007/0218426 A1 | 9/2007 | Quadling et al. ............. 433/223 |
| 2007/0269769 A1 | 11/2007 | Marchesi ..................... 433/215 |
| 2007/0281277 A1 | 12/2007 | Brajnovic |
| 2008/0038692 A1 | 2/2008 | Andersson et al. |
| 2008/0044794 A1 | 2/2008 | Brajnovic |
| 2008/0057467 A1 | 3/2008 | Gittelson |
| 2008/0070181 A1 | 3/2008 | Abolfathi et al. .................. 433/6 |
| 2008/0085489 A1 | 4/2008 | Schmitt |
| 2008/0090210 A1 | 4/2008 | Brajnovic |
| 2008/0114371 A1 | 5/2008 | Kluger |
| 2008/0118895 A1 | 5/2008 | Brajnovic |
| 2008/0124676 A1 | 5/2008 | Marotta |
| 2008/0153061 A1 | 6/2008 | Marcello ..................... 433/173 |
| 2008/0153065 A1 | 6/2008 | Brajnovic |
| 2008/0153069 A1 | 6/2008 | Holzner et al. ................ 433/223 |
| 2008/0176189 A1 | 7/2008 | Stonisch |
| 2008/0206714 A1 | 8/2008 | Schmitt ........................ 433/215 |
| 2008/0241798 A1 | 10/2008 | Holzner et al. ................ 433/223 |
| 2008/0261165 A1 | 10/2008 | Steingart et al. ................. 433/24 |
| 2008/0300716 A1 | 12/2008 | Kopelman et al. ............ 700/182 |
| 2009/0017418 A1 | 1/2009 | Gittelson |
| 2009/0026643 A1 | 1/2009 | Wiest et al. ..................... 264/16 |
| 2009/0042167 A1 | 2/2009 | Van Der Zel ................. 433/215 |
| 2009/0081616 A1 | 3/2009 | Pfeiffer ........................ 433/215 |
| 2009/0087817 A1 | 4/2009 | Jansen et al. ................. 433/223 |
| 2009/0092948 A1 | 4/2009 | Gantes |
| 2009/0098510 A1 | 4/2009 | Zhang ........................ 433/201.1 |
| 2009/0098511 A1 | 4/2009 | Zhang ........................ 433/201.1 |
| 2009/0123045 A1 | 5/2009 | Quadling et al. ............. 382/128 |
| 2009/0123887 A1 | 5/2009 | Brajnovic |
| 2009/0187393 A1 | 7/2009 | Van Lierde et al. |
| 2009/0220134 A1 | 9/2009 | Cahill et al. |
| 2009/0220916 A1 | 9/2009 | Fisker et al. ................ 433/201.1 |
| 2009/0220917 A1 | 9/2009 | Jensen ........................ 433/202.1 |
| 2009/0239197 A1 | 9/2009 | Brajnovic |
| 2009/0239200 A1 | 9/2009 | Brajnovic et al. |
| 2009/0253097 A1 | 10/2009 | Brajnovic |
| 2009/0287332 A1 | 11/2009 | Adusumilli et al. ............. 700/98 |
| 2009/0298009 A1 | 12/2009 | Brajnovic |
| 2009/0298017 A1 | 12/2009 | Boerjes et al. ................ 433/214 |
| 2009/0317763 A1 | 12/2009 | Brajnovic |
| 2009/0325122 A1 | 12/2009 | Brajnovic et al. |
| 2010/0009314 A1 | 1/2010 | Tardieu et al. |
| 2010/0028827 A1 | 2/2010 | Andersson et al. |
| 2010/0038807 A1 | 2/2010 | Brodkin et al. ................. 264/17 |
| 2010/0075275 A1 | 3/2010 | Brajnovic |
| 2010/0092904 A1 | 4/2010 | Esposti et al. |
| 2010/0173260 A1 | 7/2010 | Sogo et al. |
| 2010/0280798 A1 | 11/2010 | Pattijn et al. |
| 2011/0008751 A1 | 1/2011 | Pettersson et al. |
| 2011/0191081 A1 | 8/2011 | Malfliet et al. |
| 2011/0275032 A1 | 11/2011 | Tardieu et al. |
| 2012/0010740 A1 | 1/2012 | Swaelens et al. |

FOREIGN PATENT DOCUMENTS

| | | |
|---|---|---|
| WO | WO 94/26200 | 11/1994 |
| WO | WO99/32045 | 7/1999 |
| WO | WO 00/08415 | 2/2000 |
| WO | WO01/58379 | 8/2001 |
| WO | WO02/53055 | 7/2002 |
| WO | WO 03/024352 | 3/2003 |
| WO | WO 2004/030565 | 4/2004 |
| WO | WO2004/075771 | 10/2004 |
| WO | WO 2004/087000 | 10/2004 |
| WO | WO2004/098435 | 11/2004 |
| WO | WO2006/014130 | 2/2006 |
| WO | WO2006/062459 | 6/2006 |
| WO | WO2006/082198 | 10/2006 |
| WO | WO2007/033157 | 3/2007 |
| WO | WO2007/104842 | 9/2007 |
| WO | WO2007/129955 | 11/2007 |
| WO | WO2008/057955 | 5/2008 |
| WO | WO2008/083857 | 7/2008 |

OTHER PUBLICATIONS

Imaterialise Medical; "Surgical Guide Cookbook, Drill Guides for Every Scenario", pp. 1-87, Prior to Oct. 2010.
International Search Report dated Jun. 5, 2009 for PCT/US2009/040785.

METHOD FOR PRE-OPERATIVE VISUALIZATION OF INSTRUMENTATION USED WITH A SURGICAL GUIDE FOR DENTAL IMPLANT PLACEMENT

CROSS-REFERENCE TO RELATED APPLICATIONS

This application is a continuation of U.S. patent application Ser. No. 12/425,202, filed Apr. 16, 2009, which claims the benefit of U.S. Provisional Application No. 61/124,331 filed Apr. 16, 2008, both of which are hereby incorporated by reference in their entireties.

FIELD OF INVENTION

The present invention relates generally to use of CAD-CAM methodologies for installing dental implants. More particularly, the present invention relates to a method for pre-operative visualization of the location and positions of instrumentation that will be used with a surgical guide in placing a dental implant.

BACKGROUND OF THE INVENTION

The dental restoration of a partially or wholly edentulous patient with artificial dentition is typically done in two stages. In the first stage, an incision is made through the gingiva to expose the underlying bone. After a series of drill bits creates an osteotomy in the bone, a dental implant is placed in the jawbone for integration. The dental implant generally includes a threaded bore to receive a retaining screw holding mating components therein. During the first stage, the gum tissue overlying the implant is sutured and heals as the osseointegration process continues.

Once the osseointegration process is complete, the second stage is initiated. Here, the gum tissue is re-opened to expose the end of the dental implant. A healing component or healing abutment is fastened to the exposed end of the dental implant to allow the gum tissue to heal there around. Preferably, the gum tissue heals such that the aperture that remains generally approximates the size and contour of the aperture that existed around the natural tooth that is being replaced. To accomplish this, the healing abutment attached to the exposed end of the dental implant has the same general contour as the gingival portion of the natural tooth being replaced.

During the typical second stage of dental restoration, the healing abutment is removed and an impression coping is fitted onto the exposed end of the implant. This allows an impression of the specific region of the patient's mouth to be taken so that an artificial tooth is accurately constructed. After these processes, a dental laboratory creates a prosthesis to be permanently secured to the dental implant from the impression that was made.

In addition to the more traditional system for placing dental implants described above, some systems use guided placement of the dental implants. In these situations, a surgical plan is developed for the patient that will include the location and orientation of the implants to be installed by a surgical guide. Once the surgical plan is known, the surgical guide can be developed and, eventually, placed in the patient's mouth at the known location. The surgical guide includes openings for providing the exact placement of the drill bits used to create the osteotomy. Once the osteotomy is completed, the surgical guide may permit the dental implant to be placed through the same opening and enter the osteotomy that was guided by the surgical guide.

Surgical guides can be created by the use of a CT-scan of the patient's mouth. The CT-scan provides enough detail to develop the surgical guide by use of various methods. For example, a CT-scan can provide the details of the patient's gum tissue and/or remaining teeth so that the surgical guide can be developed based on computer-aided design (CAD) and computer-aided manufacturing (CAM). One example of the use of a CT-scan is disclosed in U.S. Patent Publication No. 2006/0093988, which is herein incorporated by reference in its entirety. This publication also describes the use of various tubes that can be placed within the surgical guide to receive the drill bits and implants.

However, some problems may occur with the development and manufacturing of the surgical guide. For example, the surgical plan may require the use of a certain sized implant, dental drill, or other components that may not fit well in the patient's mouth due to the opposing (i.e., upper or lower) teeth and/or gum tissue in the patient's mouth. Thus, the clinician may be disappointed because of the considerable amount of time and effort in planning the case, only to need a revised plan and possibly a new surgical guide. The patient, of course, is also disappointed because he or she did not receive what was expected in that visit (possibly a temporary prosthesis) and will be forced to return an additional day to complete the project.

As such, a need exists to develop an improved CAD-CAM related methodology for developing a surgical plan and a surgical guide that is used in accordance with the surgical plan.

SUMMARY OF THE INVENTION

In one aspect, the present invention is a method of manufacturing a surgical guide to be placed in a patient's mouth, comprising scanning a patient's mouth to obtain surgical-region scan data in a surgical region at which at least one dental implant is to be located, scanning a patient's mouth in the opened position to acquire dental conditions opposite from the surgical region so as to obtain opposing-condition scan data, and developing a virtual model of the patient's mouth using the surgical-region scan data and the opposing-condition scan data. The method further includes developing, with the use of the virtual model, a surgical plan that includes the location of the at least one dental implant to be placed in the mouth of the patient, developing a virtual surgical guide based on the location of the at least one dental implant and the surgical-region scan data, and checking the dimensions of instrumentation to be used with the surgical guide to ensure the instrumentation will fit within the patient's mouth by use of the opposing-condition scan data. After the checking step, the method includes obtaining final surgical-guide manufacturing information based on the virtual model, and manufacturing the surgical guide based on the final surgical-model manufacturing information.

In another aspect, a method of manufacturing a surgical guide to be placed in a patient's mouth, comprises developing a virtual model of the patient's mouth using scan data from the patient's mouth, and developing, with the use of the virtual model, a surgical plan that includes the location of multiple dental implants to be placed in the mouth of the patient. The surgical plan includes a surgical protocol of instrumentation to be used to install the multiple dental implants. The method further includes developing a virtual surgical guide based on the surgical plan and, by use of opened-mouth scan data from an opened-mouth condition from the patient's mouth, determining an available dimension from the virtual surgical guide to dental structures that are opposing each of the multiple dental implants. In response to the available dimensions being less than a dimension for the instrumentation to be used with each of the multiple dental implants, the method includes altering the surgical plan, obtaining final surgical-guide manufacturing information based on the virtual model after the altering, and manufacturing the surgical guide based on the final surgical-model manufacturing information.

According to a further aspect of the invention, a method of developing a surgical guide to be placed in a patient's mouth comprises developing, with the use of a virtual model from the patient's mouth, a surgical plan that includes the location of multiple dental implants to be placed in the mouth of the patient. The surgical plan includes a surgical protocol of instrumentation to be used to install the multiple dental implants. The method further includes developing a virtual surgical guide based on the surgical plan, and by use of opened-mouth scan data from an opened-mouth condition from the patient's mouth, determining an available dimension from the virtual surgical guide to dental structures that are opposing each of the multiple dental implants. Further, the method includes comparing the available dimensions to dimensions for the instrumentation, and altering at least one of (i) the instrumentation, (ii) the virtual surgical guide, (iii) the implant size, and/or (iv) the implant location in response to the dimensions for the instrumentation being greater than the available dimensions.

Figure 1:
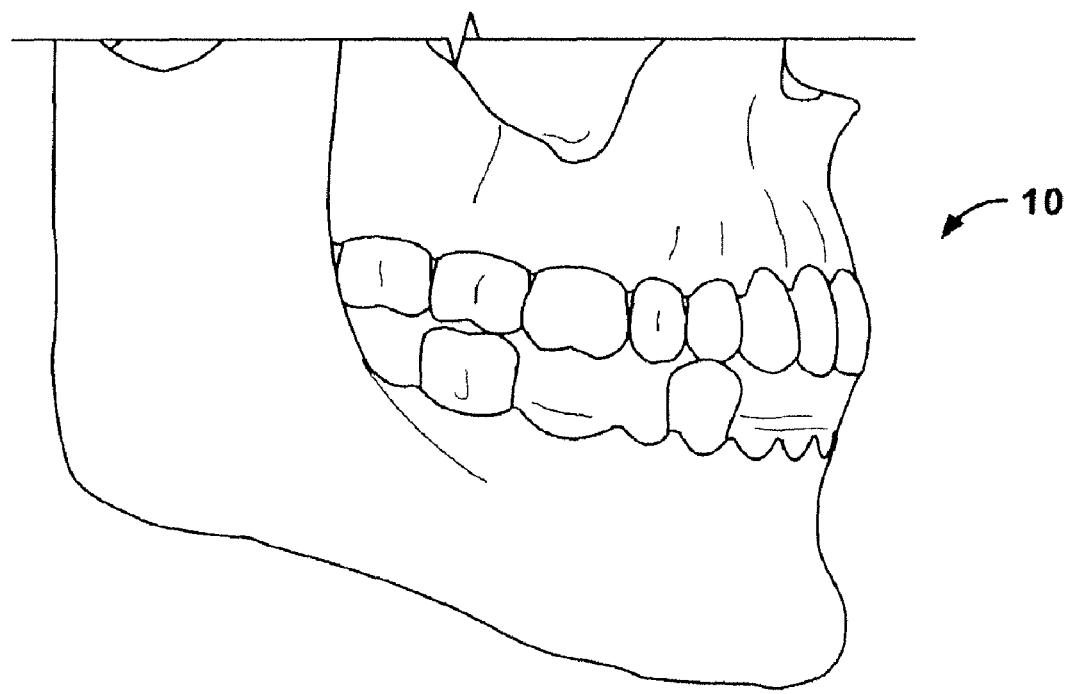
FIG. 1 is a side view of a scan of a patient's mouth with the mouth closed.

While the invention is susceptible to various modifications and alternative forms, specific embodiments thereof have been shown by way of example in the drawings and will herein be described in detail. It should be understood, however, that it is not intended to limit the invention to the particular forms disclosed but, on the contrary, the intention is to cover all modifications, equivalents, and alternatives falling within the spirit and scope of the invention as defined by the appended claims.

DESCRIPTION OF ILLUSTRATIVE EMBODIMENTS

FIG. 1 illustrates a first scan 10 of a patient's mouth with the mouth in a closed position. In this example, the patient is in need of multiple dental implants in the lower jawbone. Multiple scans may be taken from the sides to obtain scan data reflecting the entire condition of the lower jawbone. The scanning of the patient's mouth may be achieved by a CT scanner (or other scanning technologies or devices) to obtain scan data regarding the details of the bone structure, teeth and overlying gingival tissue. The first scan 10 usually involves a scanning appliance that is placed in a patient's mouth. As is known in the art, a scanning appliance is used for a partial or fully edentulous patient and includes physical shape information representing the desired prosthetic teeth in the region, usually with added material (e.g., barium sulfate) that can be picked-up by a typical CT scan.

The first scan 10 of the patient's mouth is useful in developing a surgical plan for the patient. When considering a dental surgical plan for a specific patient, the location and orientation of the implants relative to the surface of the gingival tissue, remaining teeth, and the underlying bone is important. Additionally, the maximum depth of the distal end of the implant within the bone is also important to the surgical plan, so as to avoid the sinus cavity and mandibular canal. As will be discussed in more detail below, the surgical plan will dictate the development of the surgical guide that fits snugly onto the surface of the tissue by having a negative impression that incorporates the details of the tissue surface in the patient's mouth. By the term "tissue" in the present specification, it is understood that tissue can be hard tissue (such as bone tissue or teeth) and soft tissue (such as the gingival tissue).

Figure 2:
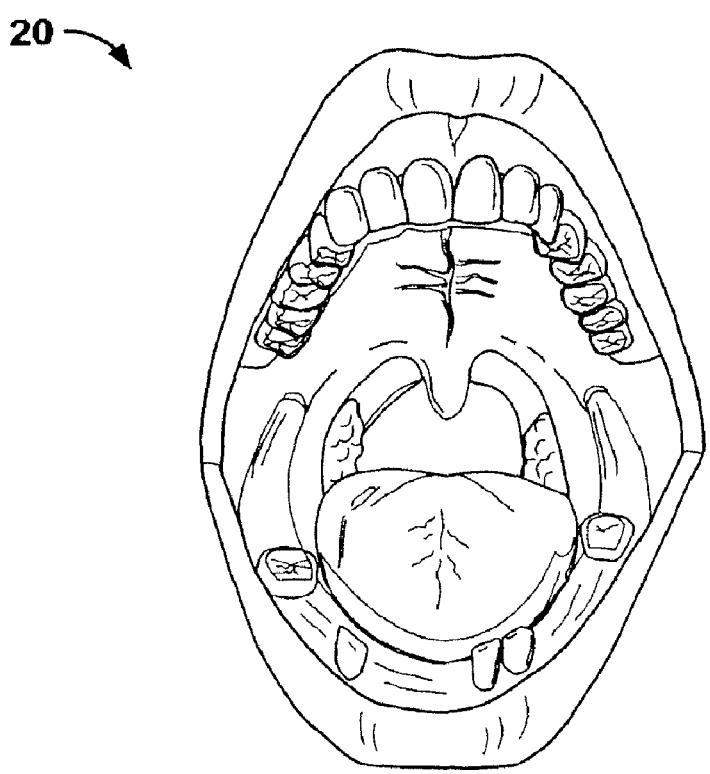
FIG. 2 is a front view of a scan of the patient's mouth with the mouth opened.

FIG. 2 illustrates a second scan 20 of the patient's mouth with the mouth in the opened position. Bite blocks may be used to assist the patient in holding his or her mouth in the opened position. If the patient is wearing a removable denture in the jaw opposing the implant-receiving region, then they would remove it during the second scan 20. Like the first scan 10 of FIG. 1, the second scan 20 may be achieved by a CT scanner that produces scan data that can be entered or downloaded into a computer for developing the surgical plan. As will be described in detail below, the second scan 20 allows the surgical plan to take into account the spatial constraints within the mouth of that particular patient. In other words, the scan second 20 provides dimensional limitations to be measured between the opposing dental structure (e.g., teeth and/or gingival tissue) and the surgical guide that will be placed on the lower jawbone in this particular patient.

Figure 3:
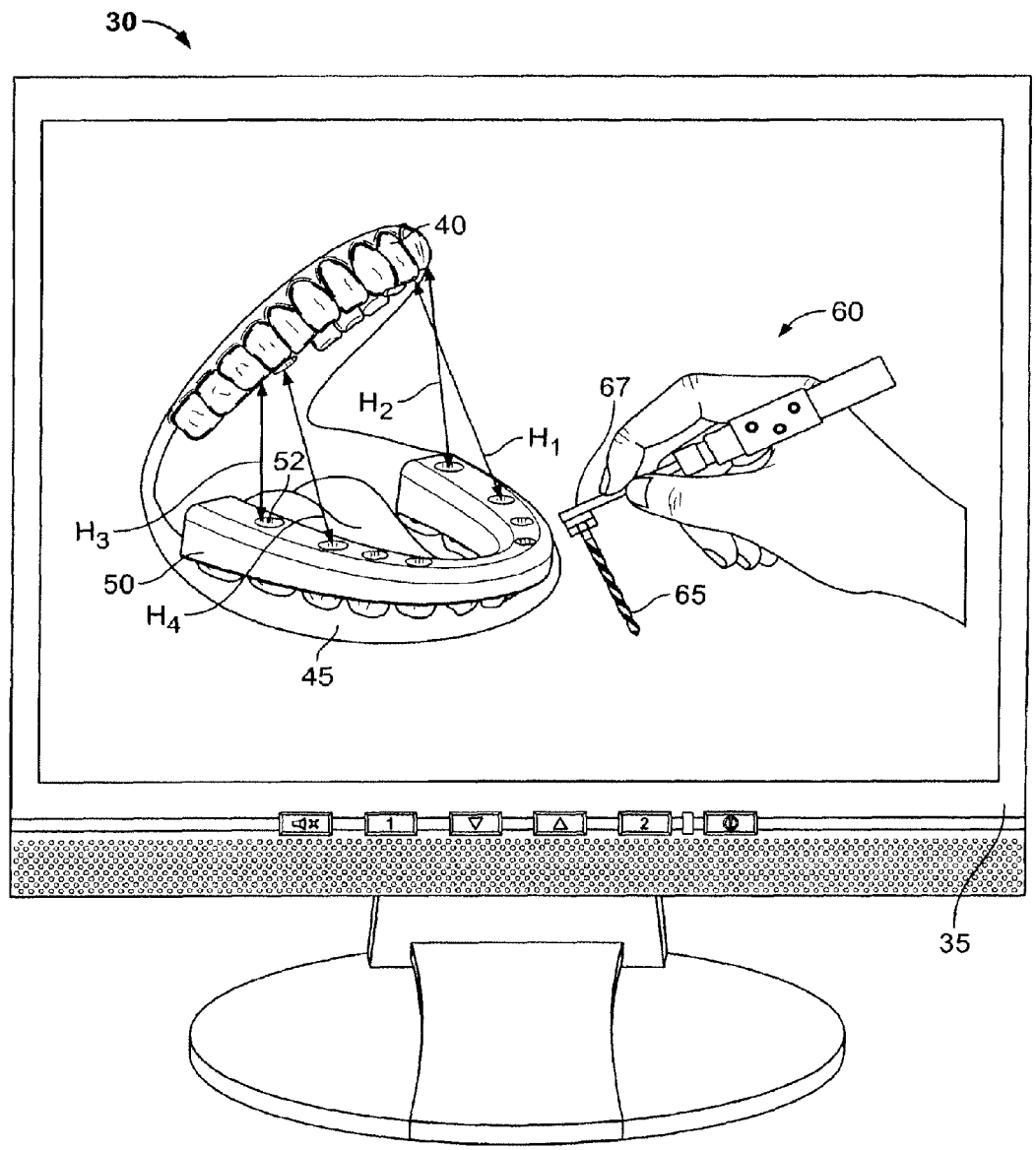
FIG. 3 illustrates a virtual image of the patient's mouth, and a surgical guide to be used in accordance to a surgical plan.
Figure 6:
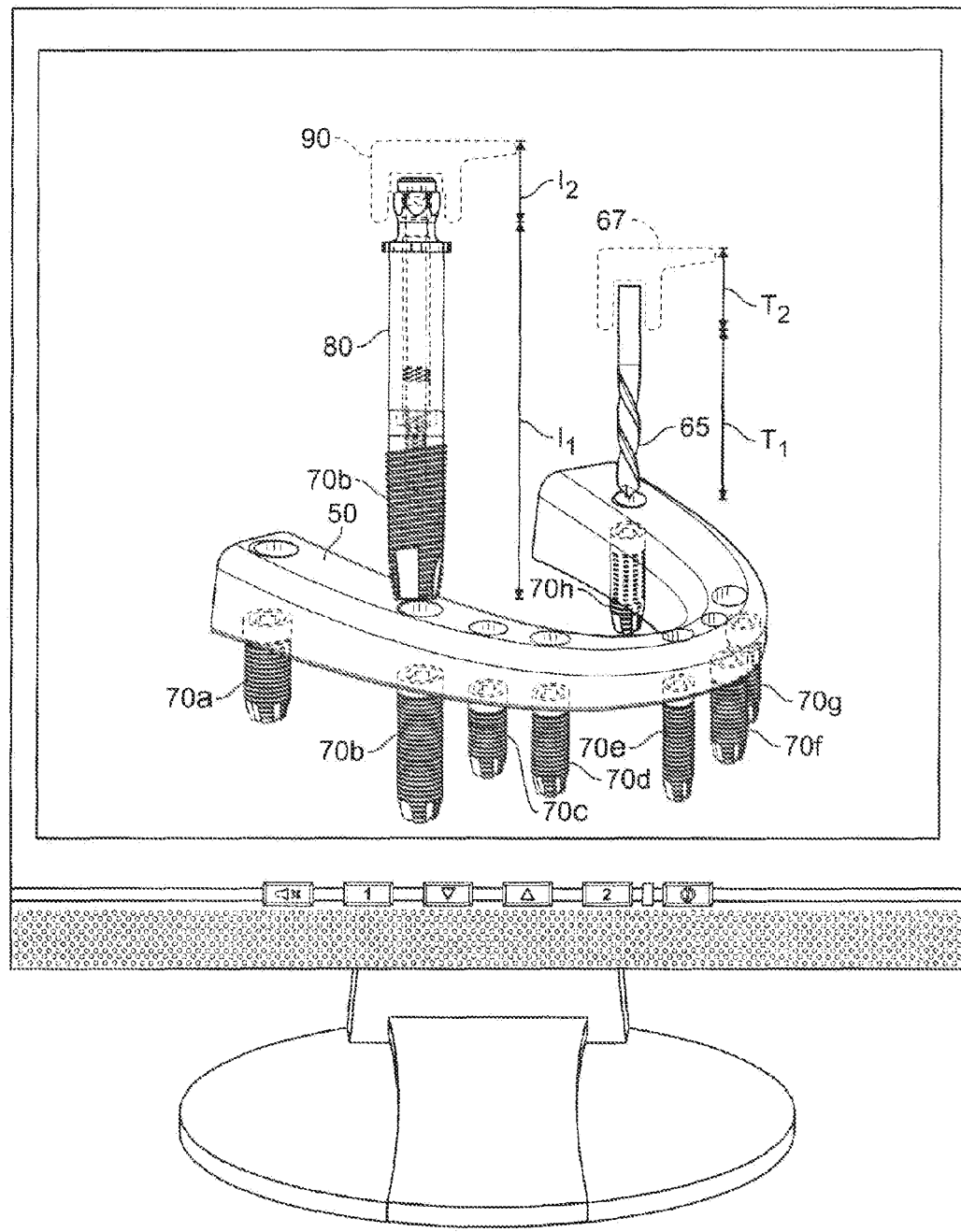
FIG. 6 illustrates a virtual image of the patient's mouth using the surgical plan, with the dental implant of FIG. 5 and the surgical drill of FIG. 4 being displayed relative to the surgical guide.

FIG. 3 illustrates a virtual model 30 of the patient's mouth that has been derived from the scan data from FIG. 1 and the opened-mouth scan data from FIG. 2. In particular, the virtual model 30 is shown on a computer display 35 and includes the upper jaw (maxillary) 40 and the lower jaw (mandible) 45. The relative dimensions between the upper jaw 40 and the lower jaw 45 are derived from the second scan 20 of the patient's mouth in the opened position. Additionally, a virtual surgical guide 50 is located on the lower jaw 45 and includes virtual openings 52 that have been established for receiving instrumentation, such as tissue punches, drill bits, counter sinks, and the dental implant that is needed for surgery. The surgical guide 50 is developed based on the desired locations in the lower jaw 45 of the dental implants as determined by the first scan 10 from the patient's mouth. Thus, prior to the display of the virtual surgical guide 50, the technician working on this case for the patient would have placed various sizes of virtual implants at ideal locations and orientations in the lower jaw 45 for properly supporting a prosthesis, such as a denture or a partial denture. The technician chooses the sizes of the dental implants, as well as their locations and angles, based on the various bone densities and underlying tissue (e.g., sinus cavity or mandibular canal) provided by the scans 10 and 20 One example of the display of the virtual implants is shown in FIG. 6.

Based on the virtual model 30, the height dimension between the top of the virtual surgical guide 50 and the opposing dental structures (in this case, teeth) can be easily determined. As shown, the height dimensions H1, H2, H3 and H4 are provided for four openings 52 in the virtual surgical guide 50 and generally correspond to the maximum height for instrumentation that will be permitted in the mouth of this particular patient due to the second scan 20 from FIG. 2. These height dimensions H1, H2, H3 and H4 are measured along the axis of the opening, which is also coincident with the axis of the planned virtual implant for that site. Thus, because the implants may not be installed in a parallel fashion due to constraints such as adjacent teeth or inadequate bone densities in certain regions of the patient's mouth, the direction of measurement of the height dimensions H1, H2, H3 and H4 may not be parallel either.

As an example, a virtual model 30 may include a hand depiction 60 of the clinician and, more importantly, a virtual drill bit 65 attached to a virtual hand piece 67 that may be needed for drilling the osteotomy for the implant to be inserted through the openings 52 corresponding to height dimension H3. If the height dimension H3 is less than the length of the instrumentation necessary to complete the implant installation on the virtual model, then alterations must be made to be surgical plan so that the instrumentation will fit within the patient's mouth at each surgical location. Examples of such alterations may include (i) changes to the size of the implant or the implant mount, (ii) changes to the location (e.g., angular orientation and/or position) of the implant in the bone, (iii) changes to the surgical guide, and/or (iv) changes to the instrumentation that is to be used for a certain implant.

The surgical planning software may utilize different points of reference other than the exterior surface of the virtual surgical guide 50 when comparing the dimensions. For example, the surgical planning software may simply place the master tubes (see FIG. 7) within the virtual model 30 and measure along the central axis from the top of the master tubes. Alternatively, the surgical planning software may utilize some rough estimation for height and thickness dimensions of certain types of surgical guides and make the determination using the estimated height and/or thickness of the surgical guide. While this latter option does not present an exact calculation, the estimation may be enough to ensure that the instrumentation will fit within the patient's mouth.

When determining whether the instrumentation will fit for each implant, the software program may simply choose the required instrument having the longest length (e.g., longest drill bit) or combination of instruments having the longest total length (e.g., implant, implant mount, surgical hand piece). If the instrument having the longest length will fit into the patient's mouth for that particular implant site, then all remaining instruments for that particular implant site should fit as well. As used herein, it should be understood that "instrument" and "instrumentation" can mean a single component (e.g. drill bit) or multiple components that are coupled together (e.g., driver plus drill bit, or implant, implant mount and surgical hand piece).

Figure 4:
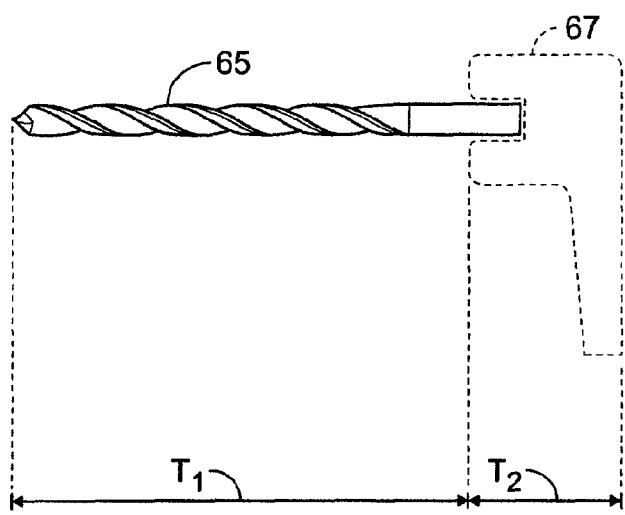
FIG. 4 is an illustration of a side view of a surgical drill that is to be used in accordance with the surgical plan.

FIG. 4 illustrates the virtual drill bit 65 and the associated power driven hand piece 67 along with their respective tool length dimensions, T1 and T2. These dimensions, T1 and T2, are stored within memory devices accessible by the software program that is used in association with the virtual model 30. These dimensions T1 and T2 can be compared against the maximum height dimensions (H1, H2, H3, H4) in the virtual model 30 to ensure that the drill bit 65 can fit within the patients mouth during the actual surgery. Similar dimensions would also be stored for other sizes of drill bits as well. Further, while FIG. 4 illustrates just one type of tool (e.g., a drill bit 65) dimensions of the various types of tools (taps, countersinks, etc.) needed for surgery would also be stored in the memory device associated with the software program that is used to conduct the virtual modeling.

Figure 5:
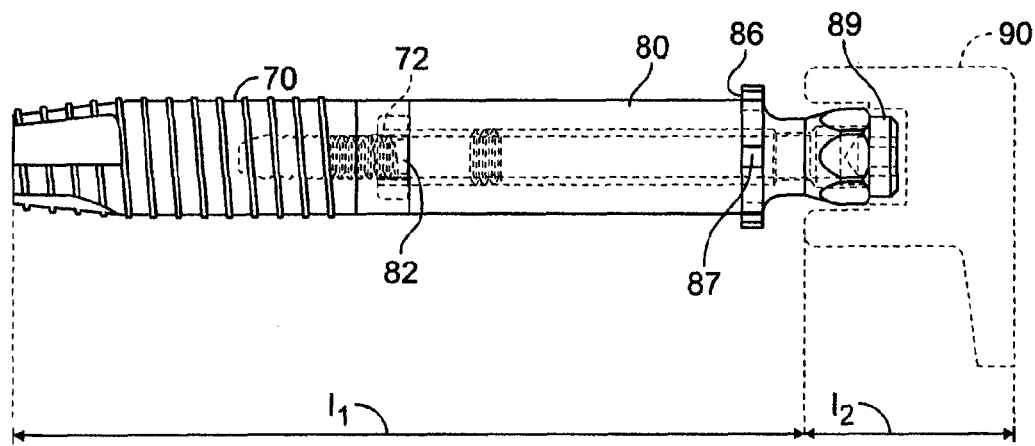
FIG. 5 is an illustration of a side view of a dental implant and a dental implant mount that are to be used in accordance with the surgical plan.

FIG. 5 illustrates a virtual dental implant 70 having an internal anti-rotational feature 72. The virtual dental implant 70 is connected to a virtual implant mount 80 with a screw such that the internal anti-rotational feature 72 mates with a corresponding anti-rotational feature 82 on the implant mount 80, just as occurs in an actual dental implant. The implant mount 80 includes an upper flange 86 with slots 87 aligned with the anti-rotational feature 82 such that the orientation of the anti-rotational feature 72 of the implant 70 can be visualized by an inspection of the slots 87. The implant mount 80 includes an upper driving portion 89 that attaches to a virtual power-driven dental device 90, such as a dental hand piece. For purposes of virtual modeling, these details of the implant 70 and implant mount 80 are not necessary. However, they have been included in FIG. 5 to provide insight as to the construction of the implant 170 and implant mount 180 as discussed in more detail below relative to FIGS. 8-10.

FIG. 5 generally illustrates the length of the combination of the virtual implant mount 80 and the implant 70 as I1 and the length of the virtual power-driven dental device 90 as I2. These dimensions, I1 and I2, are stored within a memory device accessible by the computer program that is used in association with the virtual model 30. Accordingly, these dimensions I1 and I2 can be compared against the maximum height dimensions (H1, H2, H3, H4) in the virtual model 30 to ensure that the implant 70 and its associated implant mount 80 can fit within the patient's mouth during the actual surgery. Preferably, images of the implant 70, the implant mount 80, and the power driven dental device 90 are also stored in memory device so that virtual representation of the components can be provided on the display 35 to the technician working on the virtual model.

Because the surgical plan involves the placement of the implant 70 at a certain depth below the surgical guide, the implant mount 80 is provided in various lengths. In actual surgery, the depth of penetration of the combination of the implant and the implant mount is limited by the surgical guide and, specifically, the master tubes surrounding the openings in the surgical guide that engage the flange on the implant mount, as is discussed below. Accordingly, as just one example of an alteration of the surgical plan, if the combined height of the implant 70 and its associated implant mount 80 exceeds the maximum height dimension (e.g., H3), the implant mount 80 may be selected to have a shorter length such that the top of the implant 70 does not penetrate as deep into the bone as would occur with the originally selected implant mount.

FIG. 6 illustrates an alternative display of the virtual model 30 of FIG. 3. FIG. 6 illustrates the virtual surgical guide 50 and eight virtual implants 70*a*, 70*b*, 70*c*, 70*d*, 70*e*, 70*f*, 70*g*, 70*h*. The size and locations of the virtual implants 70 are determined in accordance with the surgical plan, as dictated by the first scan 10 of the patient's lower jaw. Once the locations and sizes of the virtual implants 70 are determined, the virtual surgical guide 50 is developed with an underside surface that will fit over and mate with the patient's gingival tissue and/or remaining teeth in the lower jaw bone. FIG. 6 also illustrates the use of the drill bit 65 of FIG. 4 and the installation of a certain dental implant 70*b*. As can be seen, the overall height dimensions of these two instruments can be compared with the corresponding maximum height dimensions (shown in FIG. 3 as H2 and H4) for virtual implant 70*b* and 70*h*, respectively. Thus, it is not necessary to show the image of the upper jaw bone 40 of FIG. 3 to make the necessary comparison of dimensions.

Figure 7:
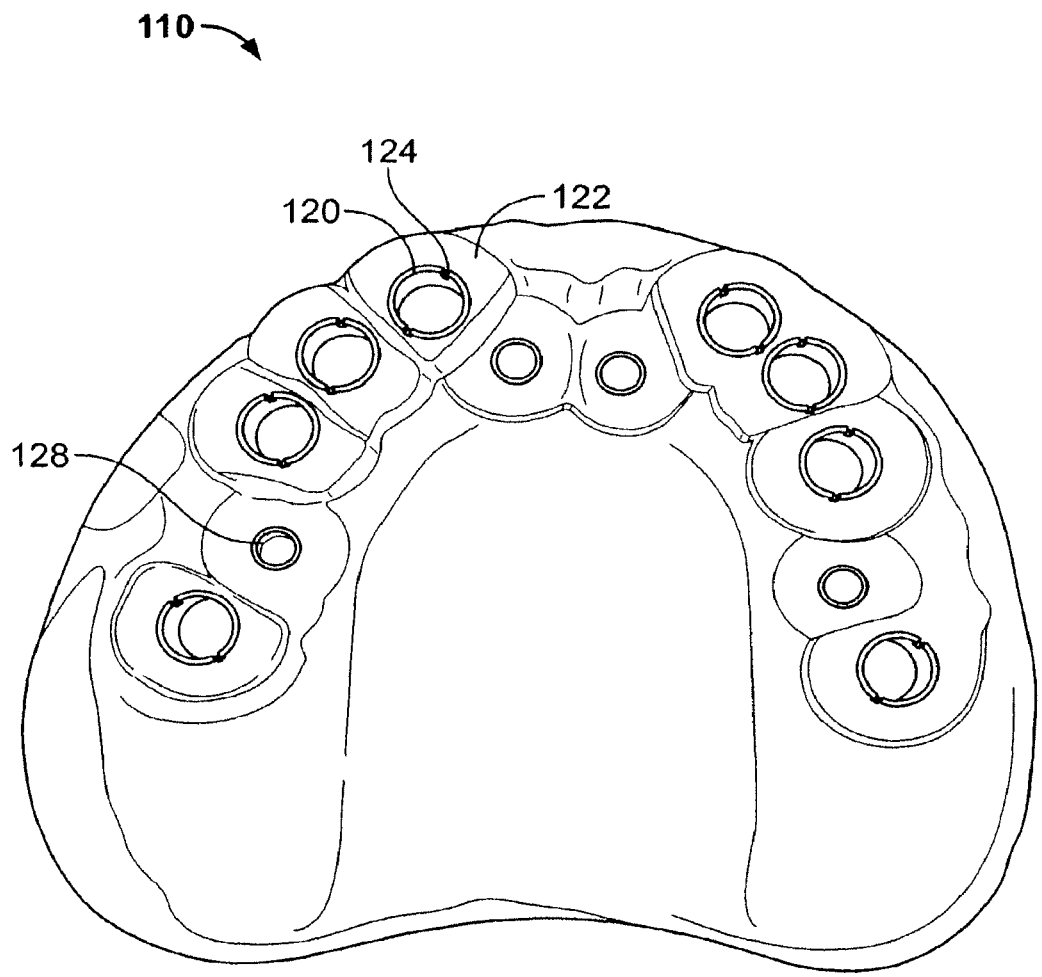
FIG. 7 illustrates the actual surgical guide of FIGS. 3 and 6 after it has been manufactured.

FIG. 7 illustrates the actual surgical guide 110 that is manufactured in accordance to standard CAD-CAM techniques based on the virtual surgical guide 50. The surgical guide 110 can be produced from various materials and techniques. One preferred method is using a rapid-prototyping technique. Because there is a need for eight implants, the surgical guide 110 includes eight openings, each of which is defined by a master tube 120 that is integrated into the material of the surgical guide 110 with the assistance of the outer roughened surface and adhesive. The master tubes 120 are located on flat surfaces 122 that are substantially flush with the top surface of the master tubes 120. The master tubes 120 have notches 124 that can be aligned with the slots 87 on the flange 86 of the implant mount 80 to dictate the exact location of the anti-rotational feature of the implant when installed in the patient's mouth. The under portion of the surgical guide 110 (not visible in FIG. 7) has a contour that follows the scan 10 (FIG. 1) of the gingival surface and/or remaining teeth in the patient's lower jaw bone. In other words, the under portion of the surgical guide 110 is a negative impression of the patient's conditions in the lower jaw bone. The surgical guide 110 also includes a plurality of openings 128 through which temporary fixation screws or pins can be placed. The temporary fixation screws or pins engage the bone and hold the surgical guide 110 in the proper location so that the surgical plan can be executed using the surgical guide 110.

As can be seen, the actual surgical guide 110 and the image of virtual surgical guide 50 on the display 30 may have a slightly different appearance because the virtual surgical guide 50 was only for determining the available dimensions. In other words, the virtual surgical guide 50 is more of a schematic illustration for purposes of determining the available dimensions. Whereas the flat surfaces 122 on the actual surgical guide 110 are variables chosen to accommodate the different lengths of the implant amounts that are available for attachment to a specific dental implant, the actual locations of the flat surfaces 122 on the virtual model can be accounted for in the dimensional comparison. Alternatively, the present invention contemplates the display of a virtual surgical guide 50 on the display 30 that is identical to the structure of the actual surgical guide 110.

Further, while the surgical guide 110 has been described relative to the use of a surgical plan with eight dental implant, the present invention is also useful for developing and installing single implants. Thus, the surgical guide 110 may be smaller such that it only covers a limited portion of the dental arch. The surgical guide 110 could be used for installing implants that support a multi-tooth prosthetic device or a full denture.

Figure 8:
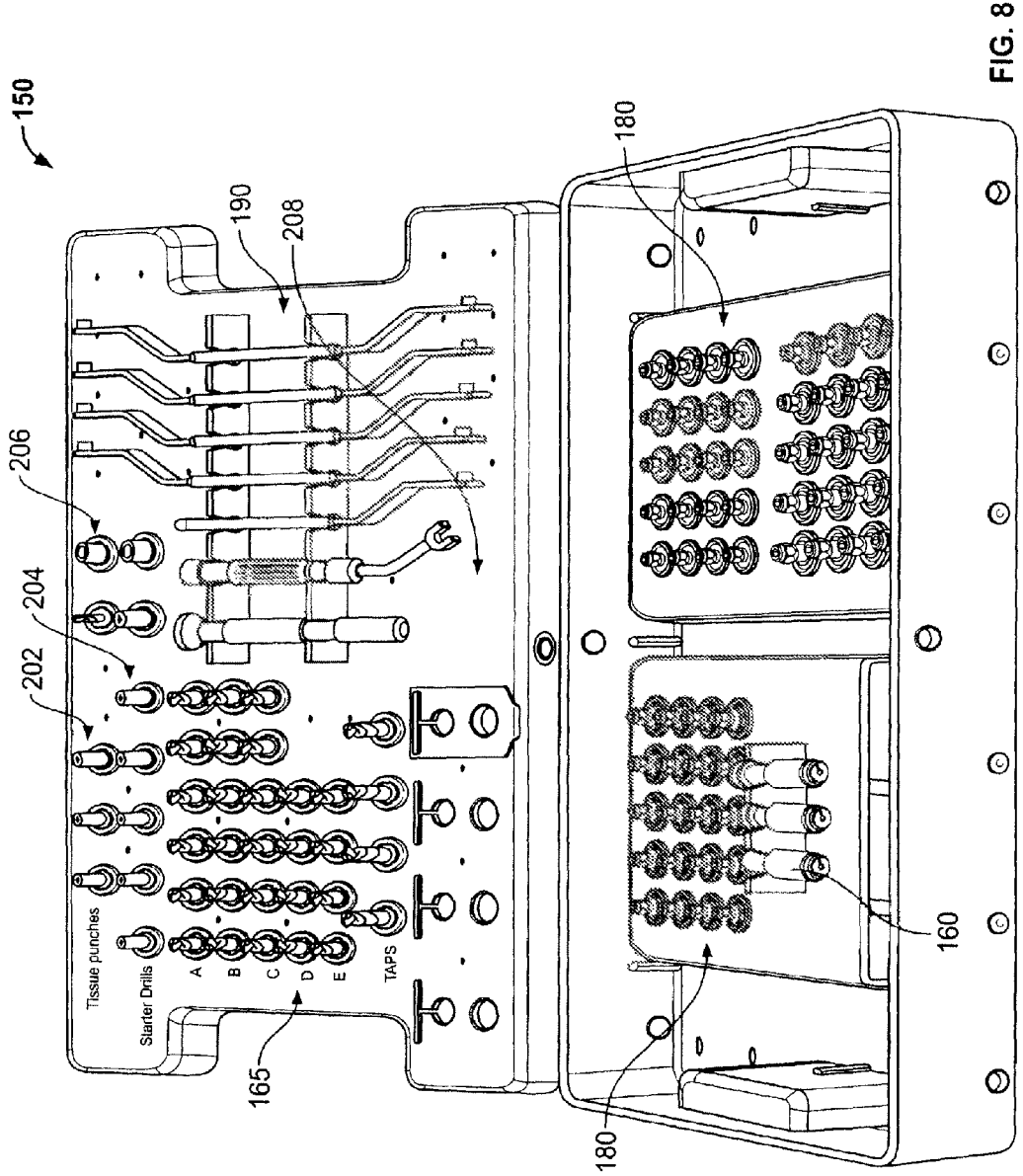
FIG. 8 illustrates a kit containing various components that are used with the surgical guide to create an osteotomy in the patient's mouth and to install a dental implant.

FIG. 8 illustrates a surgical kit 150 that contains the instrumentation that may be used to conduct the surgery with the surgical guide 110. It is these instruments that have dimensions (and preferably images) that are stored within the memory devices used with the software program for the virtual modeling. More details of the surgical kit 150 and the methods of using the surgical kit 150 in accordance with a surgical plan are disclosed in U.S. Patent Application Ser. No. 61/003,407, filed Nov. 16, 2007, and described in Biomet 3i's Navigator™ system product literature, "Navigator™ System For CT Guided Surgery Manual" that is publicly available, both of which are commonly owned and herein incorporated by reference in their entireties.

In FIG. 8, the lower portion of the surgical kit 150 includes the bone profilers 160 for shaping the bone surface at the osteotomy. The lower portion of the surgical kit 150 also includes implant mounts 180 of various sizes. For example, for each of the 3 mm, 4 mm, and 5 mm diameters of the implant mounts 180 for mating with correspondingly sized implants, the available lengths are 7.5 mm, 9.0 mm, 10.5 mm, and 12.0 mm. The surgical plan may require a set of implants having different lengths and that are positioned at different depths in the bone. Thus, the various lengths of the implant mounts 180 are needed to accommodate those dimensional variables in accordance with the surgical plan.

The upper portion of the surgical kit 150 in FIG. 8 includes drill bits 165, which may include taps for creating female threads within the osteotomy. Each of the drill bits 165 is of a different size in the length dimension (rows A, B, C, D, and E) and diametric dimension (e.g., 2.0 mm, 2.75 mm, 3.0 mm, 3.25 mm, 3.85, mm, 4.25 mm). Each drill bit 165 has a stop flange that engages the top surface of guide tubes tools 190 (discussed below) that fit within master tube 120 of the surgical guide 110 (FIG. 7) to control its depth of insertion. Thus, when the surgical plan is finally established (after comparison of the height dimensions discussed with reference to FIGS. 3-6), a specific series of drill bits 165 is chosen to be sequentially used with the surgical guide 110. For example, for a certain dental implant to be installed, the dental plan may call for the drill bits of B-2.0 mm and B-3.25 mm. The dimensions of the osteotomy are defined by the last drill bit (B-3.25 mm), which has a drill bit length dimension that accommodates the installation of that certain dental implant.

The surgical kit 150 also includes the guide-tube tools 190 that fit within the master tubes 120 to help receive the tools and implant. Each of the guide-tube tools 190 includes a handle region to be manually grasped. At both ends of the guide-tube tools 190, there are guide tubes that have a bushing-like structure. The purpose of the guide-tube tools 190 is for mating within the master tube 120 of the surgical guide 110 and, once properly seated in the master tube 120, to receive one or more of the drill bits 165 used to create the osteotomy. Because creation of the osteotomy pursuant to the surgical plan calls for a sequence of several drill bits 165 having different diameters, the guide-tube tools 190 have different diameters to engage the drill bits 165 in a relatively tight fashion to prevent the drill bit from drilling at the wrong angle. Thus, for each diameter of a drill bit 165, there is a corresponding guide-tube tool 190. Further, because the master tubes 120 in the surgical guide 110 may come in different sizes to receive different sized implants, the guide-tube tools 190 may have different outer diameters for mating with the different sized mater tubes 120. As an example, the lower two guide-tube tools 190 may only be used with a master tube 120 with a 5.1 mm inner diameter.

The surgical kit 150 further includes tissue punches 202 for removal of a known size of gingival tissue from beneath the openings in the surgical guide 110. The surgical kit 150 also includes starter drills 204, such as drill bits for creating a pilot hole and, possibly, countersinks for creating a certain shape to the opening of the osteotomy. The surgical kit 150 may include other types of tools such as implant holders 208 for holding the implants as they are mated with the correct implant mounts 180 and wrenches/drivers 206 for engaging the driving element of the implant mount 180. The surgical kit 150 is preferably made of any material that allows it to be sterilized via an autoclave.

Figure 9:
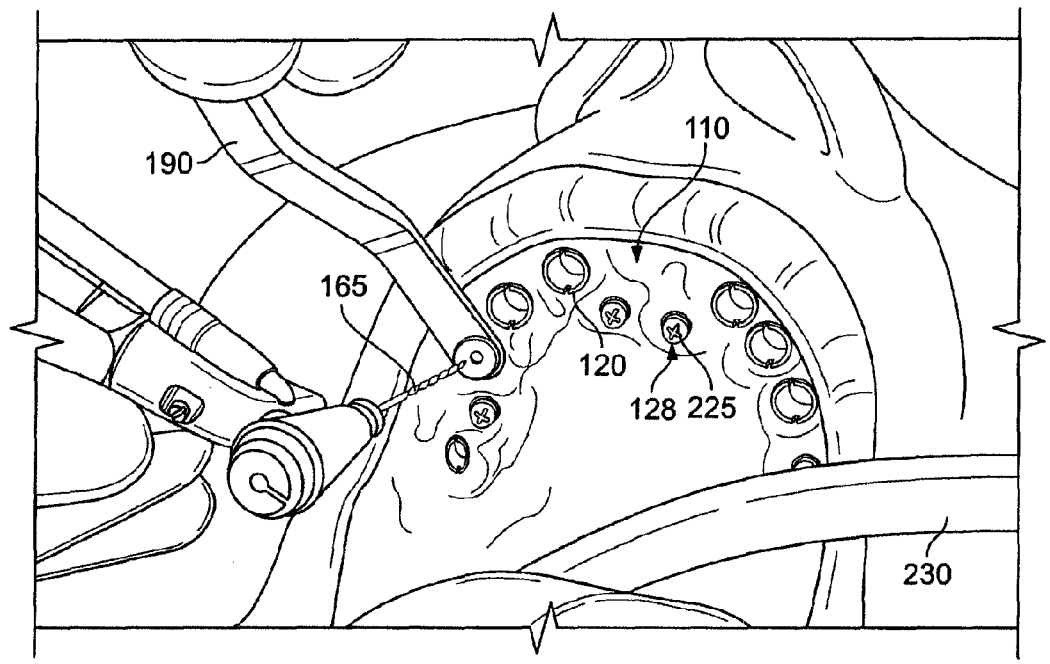
FIG. 9 illustrates the surgical guide of FIG. 7 after it has been placed in the patient's mouth, along with a drill bit that is used to develop an osteotomy.
Figure 10:
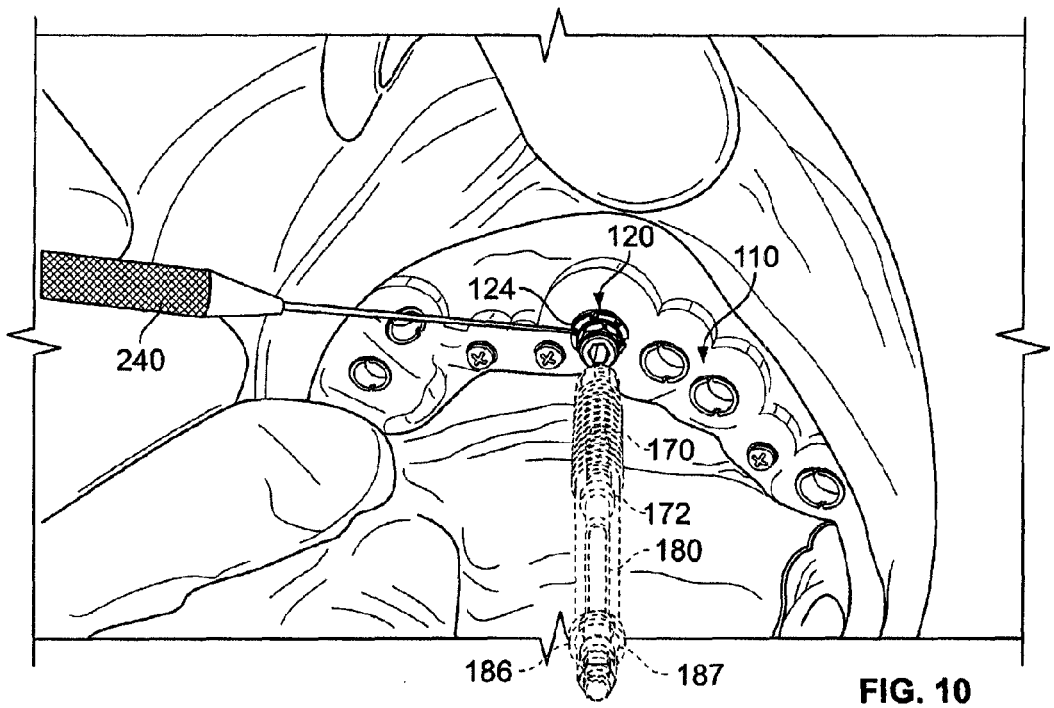
FIG. 10 illustrates the surgical guide of FIG. 7 after it has been placed in the patient's mouth, along with a dental implant that is being installed in the osteotomy.

FIGS. 9-10 provide a series of illustrations in which the surgical guide 110 is used to place the actual dental implants 170 within the patient's mouth in accordance with the pre-established dental surgical plan that located the virtual implants 70. As mentioned previously, a surgical guide 110 was created through a technique that allows it to have a negative impression of the tissue surface within the patient's lower jaw bone. Accordingly, after it has been developed, the surgical guide 110 can be installed into the patient's mouth such that it fits snugly over the gingival tissue or teeth or bone. The surgical guide 110 is held in place in the patient's mouth by use of small, temporary fixations screws or pins 225 that fit through the openings 128 in the surgical guide 110. Once it is fixed in place, the surgical guide 110 is used to conduct surgery in accordance to the dental plan discussed above.

FIG. 9 illustrates the use of a certain guide-tube tool 190 that fits within one of the master tubes 120 of the surgical guide 110. The guide-tube tool 190 then receives a first drill bit 165 (for example, a pilot drill) that is powered by a driver. Because of the various fluids and materials that can build up during the surgery within patient's mouth, a suction tube 230 is often employed.

FIG. 10 illustrates the placement of one of the dental implants 170, which has been attached to a specifically-sized implant mount 180 in accordance to the surgical plan. In particular, the implant 170 has been screwed into the bone by use of a tool that engages the driving element of the implant mount 180. Because the underlying anti-rotational feature 172 of the implant 110 (the same as anti-rotational feature 72 of the implant 70 in FIG. 5) is aligned with the notch 187 of the flange 186 of the implant mount 180, the non-rotational feature 172 is oriented in the exact location defined by the dental surgical plan by aligning the notch 187 of the implant mount 180 with the notch 124 in the master tube 120. A tool 240 may be used to detect the alignment of the notch 124 and the notch 187. As discussed previously, because the implant mount 180 has a known length, the exact depth of the implant 170 within the osteotomy is also known, as defined by the dental plan for that patient.

Figure 11:
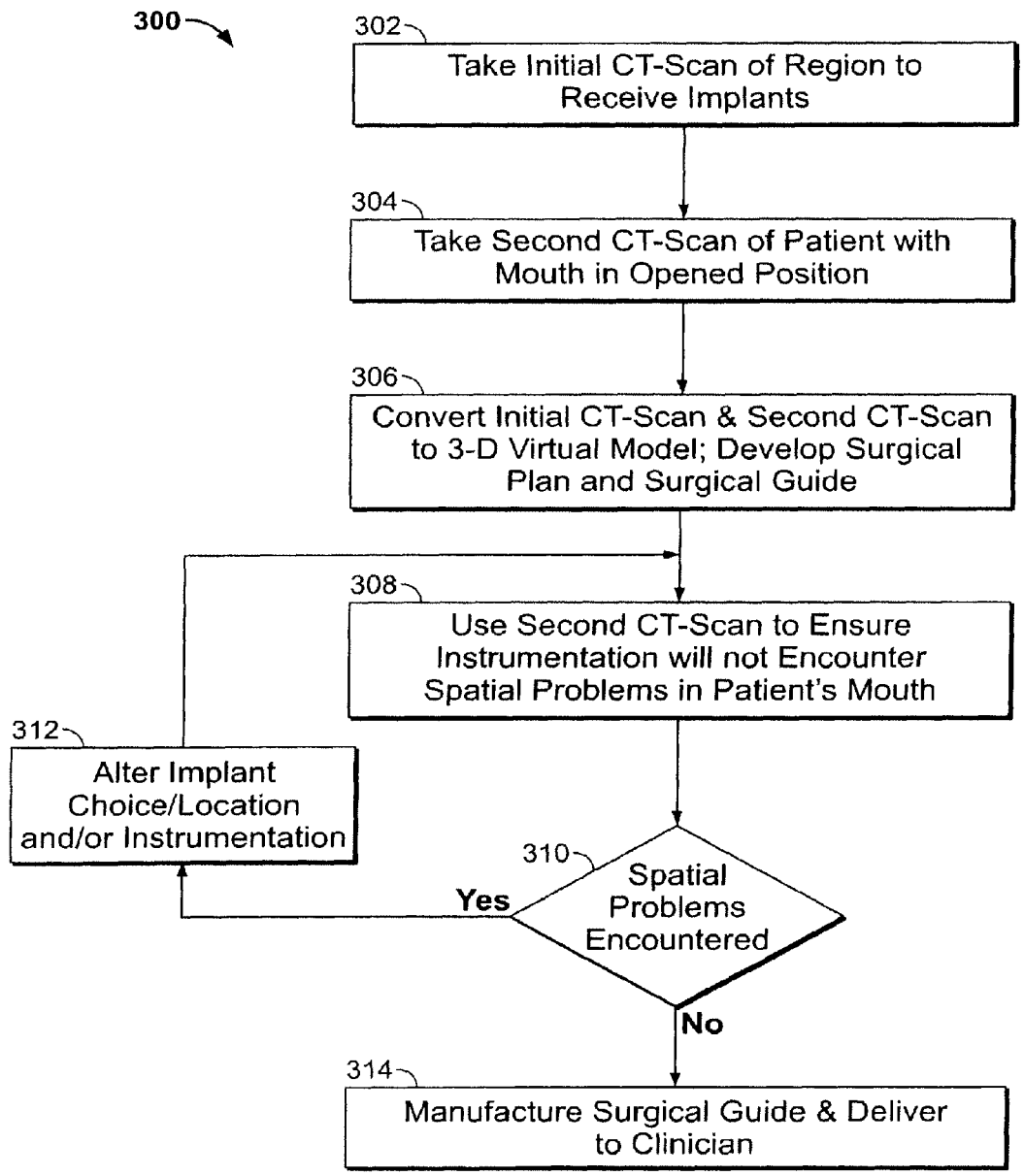
FIG. 11 illustrates a flow chart of the process used to develop the surgical plan and the surgical guide.

FIG. 11 illustrates a flow chart 300 for use in creating a surgical guide in accordance with the present invention. At step 302, a CT scan is taken of the region in the patient's mouth that will receive the dental implants. At step 304, a CT scan is taken of the patient's mouth in the opened position. Next, at step 306, the data from the CT scans at step 302 and 304 is then imported into computer modeling software and used to develop a 3-D virtual model of the patient's mouth. The data from the CT scans at step 302 and 304 is then merged, via a shape-matching algorithm to develop a unitary virtual model. The shape-matching algorithm, as is commonly known in CAD/CAM and scanning systems, utilizes common features (e.g., bone, markers, teeth, scanning appliances, etc.) in the two scans to locate the relative position of one set of data to the other set of data. With the use of the virtual model created by the CT scans at step 302 and 304, the surgical plan is developed along with the surgical guide to be used with the surgical plan at step 306.

Based on the data from the second CT scan of step 304, the instrumentation suggested for use in accordance with the surgical plan can be compared against the available dimensions within the patient's mouth. Thus, at step 308, the dimensions of the instrumentation suggested for use with each implant in the surgical plan (according to system parameters) are compared against the available dimensions to ensure that there will be no spatial problems encountered in the patient's mouth. Accordingly, at step 310, if spatial problems are encountered, the surgical plan must be altered to ensure that no spatial problems will be encountered during the actual surgery in the patient's mouth. As such, at step 312, for any implant that has encountered a problem, the alterations related to the implant or the suggested instrumentation can occur. Examples of such alterations may include (i) changes to the size of the implant or the implant mount, (ii) changes to the location (e.g., angular orientation and/or position) of the implant in the bone, (iii) changes to the surgical guide, and/or (iv) changes to the instrumentation that is to be used for a certain implant.

Once the alteration of the surgical plan at step 312 has occurred, the information from the second CT scan is again used to ensure that the newly suggested instrumentation (based on the alteration of the surgical plan) will not cause spatial problems in the patient's mouth (i.e., step 308 is repeated). If no spatial problems are encountered at step 310, then manufacturing data for the virtual surgical guide can be developed for use in manufacturing the actual surgical guide, as in step 314. Once the actual surgical guide is manufactured, it can then be delivered to the clinician for placement in the patient's mouth (as in step 314) and for conducting surgery in accordance with the surgical plan derived from the virtual model.

Considering the various alterations that are possible at step 312, it should be noted that some of those possible alterations inherently involve a change to the virtual surgical guide 50. For example, changes to the position and/or orientation of the virtual implant 70 will also include changes to the openings corresponding to the master tubes 120 in the virtual surgical guide 50. On the other hand, some alterations may not require a change to the virtual surgical guide 50. For example, if a shorter implant or a shorter implant mount is selected as an alteration, no alterations to the virtual surgical guide 70 may be needed. In a further possible arrangement, only an alteration to the virtual surgical guide may be necessary. For example, a spatial problem may be so minor that simply altering the thickness of the surgical guide may be enough to alleviate the problem. Or, changing the angle of an opening in the virtual surgical guide may be enough to alleviate the problem.

In an alternative embodiment, the present invention contemplates the use of only a single scan with the mouth in the opened position. In other words, the single scan gathers enough information about the implant installation site, while also providing enough information about the opened-mouth condition that allows for the determination of spatial limitations. Thus, when considering FIG. 11, step 302 would be unnecessary and, in step 306, the virtual model would be developed by the single scan of the opened mouth.

If a single scan is used, then a need exists for providing a bite registration between the upper jaw conditions and the lower jaw conditions. One way to accomplish this task is by the use of a scanning appliance that has been modified to include material for the bite registration. The scanning appliance for the patient may include a layer of barium sulfate of the modeled teeth structures such that the teeth structures are identified by the CT scan. Next, impression material is added to the region of the scanning appliance at which the bite registration for the opposing teeth is expected. The patient would then close his or her mouth to create the bite registration in the impression material on the scanning appliance. Once hardened, the impression material is then provided with a layer of barium sulfate (or other material that is identifiable by the scan) at a different concentration level so that the patient's bite registration can be independently identified in the single CT scan and distinguished from the teeth structure on the scanning appliance. More information about CT-scanning and the use of scanning appliances can be found in the product brochure entitled "Simplant® SurgiGuide Cookbook" from Materialise US Clinical Services, Inc., Glen Burnie, Md., which is herein incorporated by reference in its entirety. After the patient undergoes the single scan with the mouth in the opened position using the scanning device having the bite registration, a virtual model of the patient's mouth in the closed position can be created by merging the upper and lower conditions with a shape-matching algorithm. The surgical plan can be developed, and the instrumentation to be used in the surgical plan can be checked for spatial constraints, as described above. As such, the present invention contemplates the use of a scanning appliance that has been modified to include a representation of a bite registration.

It should also be noted that present invention contemplates the use of virtual modeling to develop a surgical plan that does not require the use of a surgical guide. In other words, the CT-scans (or CT-scan) are used by the clinician to develop a virtual model indicating appropriate locations for the implants based on the conditions in the patient's mouth. While no surgical guide is developed to dictate the exact angular position and location of each implant in the patient's mouth, the virtual model is still used for pre-operative visualization to determine whether instrumentation will fit into the patient's mouth to place the implants. If the spatial constraints indicate that instrumentation will not fit, then changes to the instrumentation or the surgical plan may be needed.

Similarly, the present invention contemplates the use of virtual modeling to develop a non-dental implant surgical plan that measures whether instrumentation will fit within the patient's mouth to accomplish the non-dental implant surgical plan. Again, the virtual model is used for pre-operative visualization to determine whether instrumentation will fit into the patient's mouth when performing the non-dental implant surgical plan.

While particular embodiments and applications of the present invention have been illustrated and described, it is to be understood that the invention is not limited to the precise construction and compositions disclosed herein and that various modifications, changes, and variations may be apparent from the foregoing descriptions without departing from the spirit and scope of the invention as defined in the appended claims.

What is claimed is:

1. A method of manufacturing a surgical guide to be placed in a patient's mouth, comprising:
    scanning a patient's mouth to obtain surgical-region scan data in a surgical region at which at least one dental implant is to be located and dental conditions opposite from the surgical region so as to obtain opposing-condition scan data;
    developing a virtual model of the patient's mouth using the surgical-region scan data and the opposing-condition scan data;
    checking the dimensions of instrumentation to be used with the surgical guide using the opposing-condition scan data to ensure the instrumentation will fit within the patient's mouth;
    after the checking step, obtaining final surgical-guide manufacturing information based on the virtual model; and
    manufacturing the surgical guide based on the final surgical-model manufacturing information.

2. The method of claim 1, further including placing the surgical guide in the patient's mouth and installing the at least one dental implant through an opening in the surgical guide.

3. The method of claim 2, wherein the surgical guide is made of a polymeric material and includes a master tube that is made from a metal, the master tube being embedded in the polymeric material and providing the opening.

4. The method of claim 3, wherein the installing the at least one dental implant includes developing an osteotomy with a plurality of drill bits that fit through the opening prior to the installation of the at least one dental implant, each of the plurality of drill bits being the instrumentation used with the virtual model to ensure proper fitting within the patient's mouth.

5. The method of claim 1, wherein the instrumentation includes a plurality of drill bits that are illustrated in the virtual model to ensure proper fitting.

6. The method of claim 1, wherein the instrumentation includes a combination of an implant mount and the at least one dental implant attached thereto, the combination being illustrated in the virtual model to ensure proper fitting.

7. The method of claim 1, wherein in response to the checking of the dimensions of the instrumentation indicating an unworkable condition, altering the instrumentation so that altered instrumentation fits within the patient's mouth.

8. The method of claim 1, further comprising developing a virtual surgical guide based on the location of the at least one dental implant and the surgical-region scan data.

9. The method of claim 8, wherein in response to the checking of the dimensions of the instrumentation indicating an unworkable condition, altering the location of the at least one dental implant and altering the virtual surgical guide so that the instrumentation fits within the patient's mouth.

10. The method of claim 1, further comprising developing, with the use of the virtual model, a surgical plan that includes the location of the at least one dental implant to be placed in the mouth of the patient.

11. The method of claim 10, wherein developing the surgical plan further includes determining the instrumentation to be used in installing the implant.

12. The method of claim 11, wherein in response to the checking of the dimensions of the instrumentation indicating an unworkable condition, altering the surgical plan so that the instrumentation fits within the patient's mouth.

13. The method of claim 1, further comprising displaying the virtual model on a display.

14. The method of claim 1, further comprising displaying the instrumentation on a display.

15. A method of developing a surgical plan for placing a dental implant in a patient's mouth, the method comprising:
    scanning a patient's mouth in an opened position to acquire surgical-region scan data and opposing-condition scan data;
    developing a virtual model of the patient's mouth using the surgical-region scan data and the opposing-condition scan data, the virtual model indicating a location for the dental implant;
    using the virtual model to determine whether instrumentation to be used in an actual surgery will fit within the patient's mouth; and
    after determining whether the instrumentation will fit, developing the surgical plan that includes the location of the dental implant to be placed in the mouth of the patient and a surgical protocol of the instrumentation to be used to install the dental implant.

16. The method of claim 15, wherein the instrumentation includes a plurality of drill bits having instrumentation dimensions used within the virtual model to ensure proper fitting.

17. The method of claim 15, wherein the instrumentation includes a combination of an implant mount and the dental implant attached thereto, the combination having instrumentation dimensions used within the virtual model to ensure proper fitting.

18. The method of claim 15, wherein the opposing-condition scan data provides spatial constraint data including an available dimension measured from a surgical region of the patient's top or bottom jaw to an opposing region of the other of the patient's top or bottom jaw.

19. The method of claim 18, further comprising altering the surgical plan by altering the instrumentation so that altered instrumentation has a dimension that is less than the available dimension.

20. The method of claim 15, further comprising displaying the virtual model on a display.

21. The method of claim 20, further comprising manufacturing a surgical guide to be placed in the patient's mouth based on the surgical plan.

22. The method of claim 15, further comprising displaying the instrumentation on a display.

23. The method of claim 22, further comprising manufacturing a surgical guide to be placed in the patient's mouth based on the surgical plan.

* * * * *